United States Patent
Caquias et al.

(10) Patent No.: US 10,500,133 B2
(45) Date of Patent: Dec. 10, 2019

(54) MULTI-MIX INFUSION BAG

(71) Applicants: Tomas A. Caquias, Brownsville, TX (US); Jesus A. Caquias, Brownsville, TX (US)

(72) Inventors: Tomas A. Caquias, Brownsville, TX (US); Jesus A. Caquias, Brownsville, TX (US)

(*) Notice: Subject to any disclaimer, the term of this patent is extended or adjusted under 35 U.S.C. 154(b) by 535 days.

(21) Appl. No.: 14/804,071

(22) Filed: Jul. 20, 2015

(65) Prior Publication Data

US 2016/0015889 A1    Jan. 21, 2016

Related U.S. Application Data (60) Provisional application No. 62/026,171, filed on Jul. 18, 2014.

(51) Int. Cl.
| | | |
|---|---|---|
| *A61J 1/20* | (2006.01) | |
| *A61J 1/10* | (2006.01) | |
| *A61J 1/14* | (2006.01) | |
| *A61M 5/14* | (2006.01) | |

(52) U.S. Cl.
CPC ............ *A61J 1/2003* (2015.05); *A61J 1/10* (2013.01); *A61J 1/1406* (2013.01); *A61J 1/1475* (2013.01); *A61J 1/2006* (2015.05); *A61J 1/2093* (2013.01); *A61M 5/1407* (2013.01); *A61M 5/1408* (2013.01); *A61J 1/1462* (2013.01)

(58) Field of Classification Search
CPC .......... A61J 1/2003; A61J 1/10; A61J 1/1406; A61J 1/1462; A61J 1/1475; A61J 1/2006; A61J 1/2093; A61M 2202/0007; A61M 5/14; A61M 5/1407; A61M 5/1408
See application file for complete search history.

(56) References Cited

U.S. PATENT DOCUMENTS 5,267,646 A * 12/1993 Inoue ................. A61J 1/2093
                                                        206/204
6,135,632 A    10/2000 Flint
9,334,098 B1 *  5/2016 Hughes ............. B65D 81/3266
(Continued)

FOREIGN PATENT DOCUMENTS

| CN | 201020549537 | 5/2010 |
| CN | 201840664 | 5/2011 |
| CN | 103800199 | 5/2014 |

OTHER PUBLICATIONS

Caquias et al., Multi-Mix Infusion Bag, Patent Cooperation Treaty Application Serial No. PCT/US15/41178, filed Jul. 20, 2015, International Search Report and Written Opinion dated Oct. 29, 2015.

*Primary Examiner* — Brandy S Lee
(74) *Attorney, Agent, or Firm* — Schmeiser, Olsen & Watts, LLP (57) ABSTRACT

A multi-mix infusion bag is provided. The multi-mix infusion bag includes a lower portion and an upper portion. The lower portion has a lower chamber and the upper portion includes a plurality of chambers. Each chamber is separated and contains a fluid agent. The multi-mix infusion bag is configured to transfer each fluid agent within each chamber of the upper portion into the lower chamber for mixing. The multi-mix infusion bag may include dispensing devices associated with each chamber, wherein the dispensing devices operate to transfer the fluid agents into the lower chamber for mixing.

14 Claims, 9 Drawing Sheets

(56) References Cited

U.S. PATENT DOCUMENTS

2005/0215976 A1     9/2005   Wallen  
2005/0224372 A1 * 10/2005   Sasso .................... A61J 1/2093  
                                                            206/219

\* cited by examiner

MULTI-MIX INFUSION BAG

CROSS REFERENCE TO RELATED APPLICATION[S]

This application claims priority to U.S. Provisional Patent Application entitled "MULTI-MIX INFUSION BAG," Ser. No. 62/026,171, filed Jul. 18, 2014, the disclosure of which is hereby incorporated entirely herein by reference.

BACKGROUND OF THE INVENTION

Technical Field

This invention relates generally to an infusion bag and more particularly to a multi-mix infusion bag.

State of the Art

The use of infusion bags has been critical in the medical industry. These bags have been the means of delivering many types of fluids to patients, for example for various types of intravenous therapies, such as, but not limited to, correcting electrolyte imbalances, delivering medications, transfusing blood, or replacing fluid to correct conditions such as dehydration.

A conventional infusion bag typically contains only one solution. Further, it is not able to prevent issues of improper mixing by an administrator (such as a medical professional or pharmacy employee) due to human error. Any mixture of components must also be prepared on site, which results in a risk of contamination. This risk is much greater due to the various sites (location not being sterile) that the mixture will be prepared in. A conventional infusion bag also does not assure the quality of its contents, does not minimalize variance of the mixed contents (the mixer is at times inconsistent), and administration is more cumbersome because the mixture must be prepared before administering a solution to the patient. These drawbacks make it difficult to provide a mixture of components in an infusion bag for delivery to a patient.

Accordingly, there is a need for an improved infusion bag to address these drawbacks.

SUMMARY OF EMBODIMENTS OF THE INVENTION

The present invention relates to a multi-mix infusion bag, wherein the infusion bag has a capability to store multiple components that can be later mixed within the same bag.

An embodiment includes a multi-mix infusion bag comprising a lower portion and an upper portion. The lower portion may have a lower chamber. The upper portion may comprise a plurality of chambers, wherein each chamber is separated and contains a fluid agent, and wherein the multi-mix infusion bag is configured to transfer each fluid agent within each chamber of the upper portion into the lower chamber for mixing.

Another embodiment includes a multi-mix infusion bag comprising a separate lower portion and an upper portion. The lower portion may have a lower chamber. The upper portion may comprise four chambers, wherein each chamber is separated and contains a fluid agent in a stored condition, and wherein the multi-mix infusion bag is moveable into a dispensing condition, wherein each fluid agent within each chamber of the upper portion is transferred into the lower chamber for mixing.

Yet, another embodiment includes a method of using a multi-mix infusion bag. The method may comprise providing a multi-mix infusion bag having a plurality of chambers, wherein each chamber is pre-filled with a fluid agent in a stored condition; activating dispensing devices of the multi-mix infusion bag to move the multi-mix infusion bag into a dispensing condition, wherein the fluid agent in each chamber is transferred into a lower chamber; mixing the fluid agents to form a mixed fluid; and dispensing the mixed fluid to a patient.

The foregoing and other features and advantages of the present invention will be apparent from the following more detailed description of the particular embodiments of the invention, as illustrated in the accompanying drawings.

BRIEF DESCRIPTION OF THE DRAWINGS

A more complete understanding of the present invention may be derived by referring to the detailed description and claims when considered in connection with the Figures, wherein like reference numbers refer to similar items throughout the Figures, the Figures are not necessarily drawn to scale, and:

DETAILED DESCRIPTION OF EMBODIMENTS OF THE INVENTION

As discussed above, embodiments of the present invention relate to a multi-mix infusion bag comprising multiple agents stored separately and mixed within the infusion bag prior to dispensing. Embodiments of the invention can be sold pre-filled and ready to use; reduces risk of human error; reduces risk of contamination; increases ease of administration; simplifies the process of administrating infusions intravenously; protects content from oxidation; assures accurate administration; permits little to no variance between the mixtures; increases the contents shelf life; and prevents contents from reacting adversely and prematurely.

Figure 1:
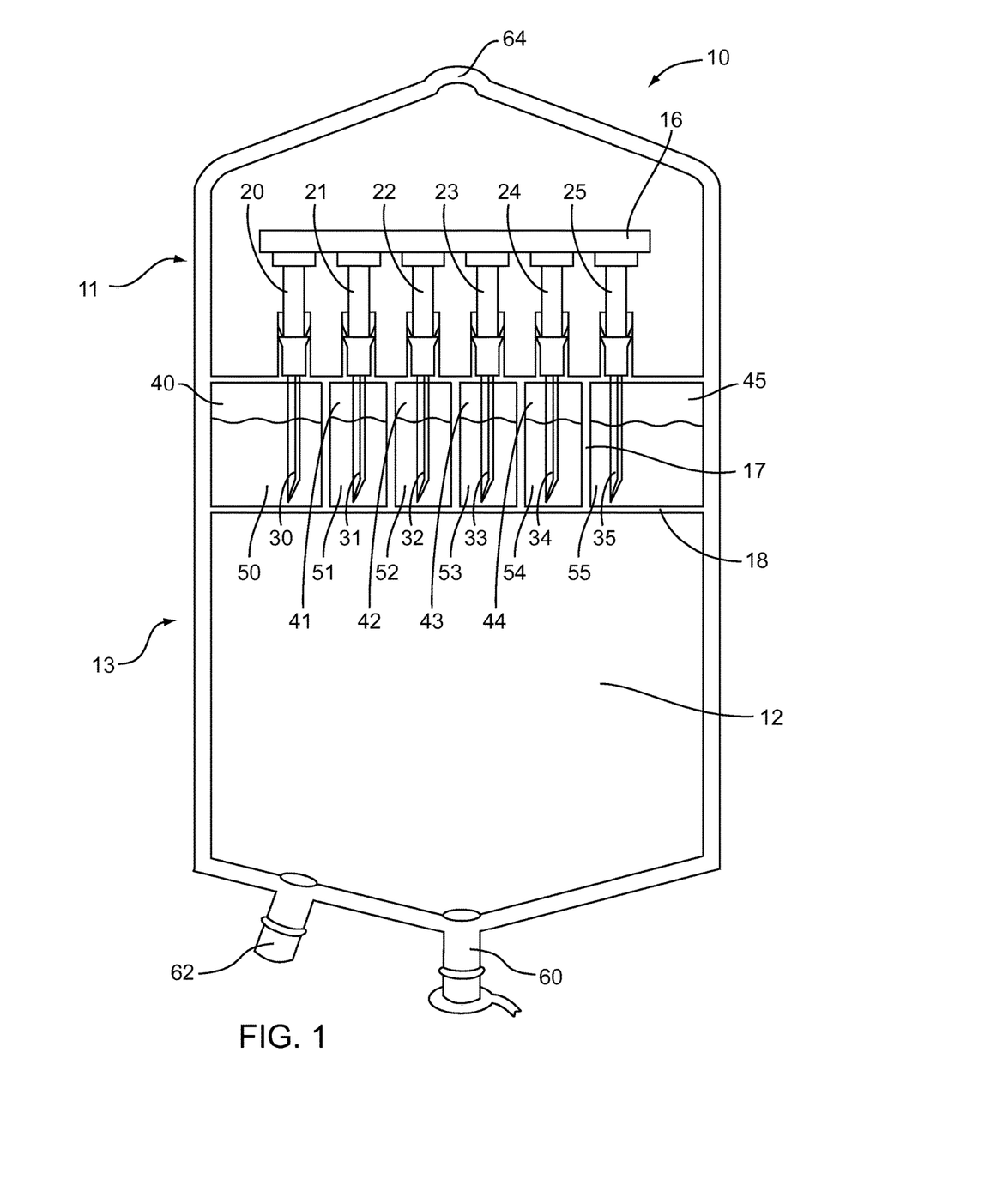
FIG. 1 is a front view of a multi-mix infusion bag with agents compartmentalized.
Figure 3:
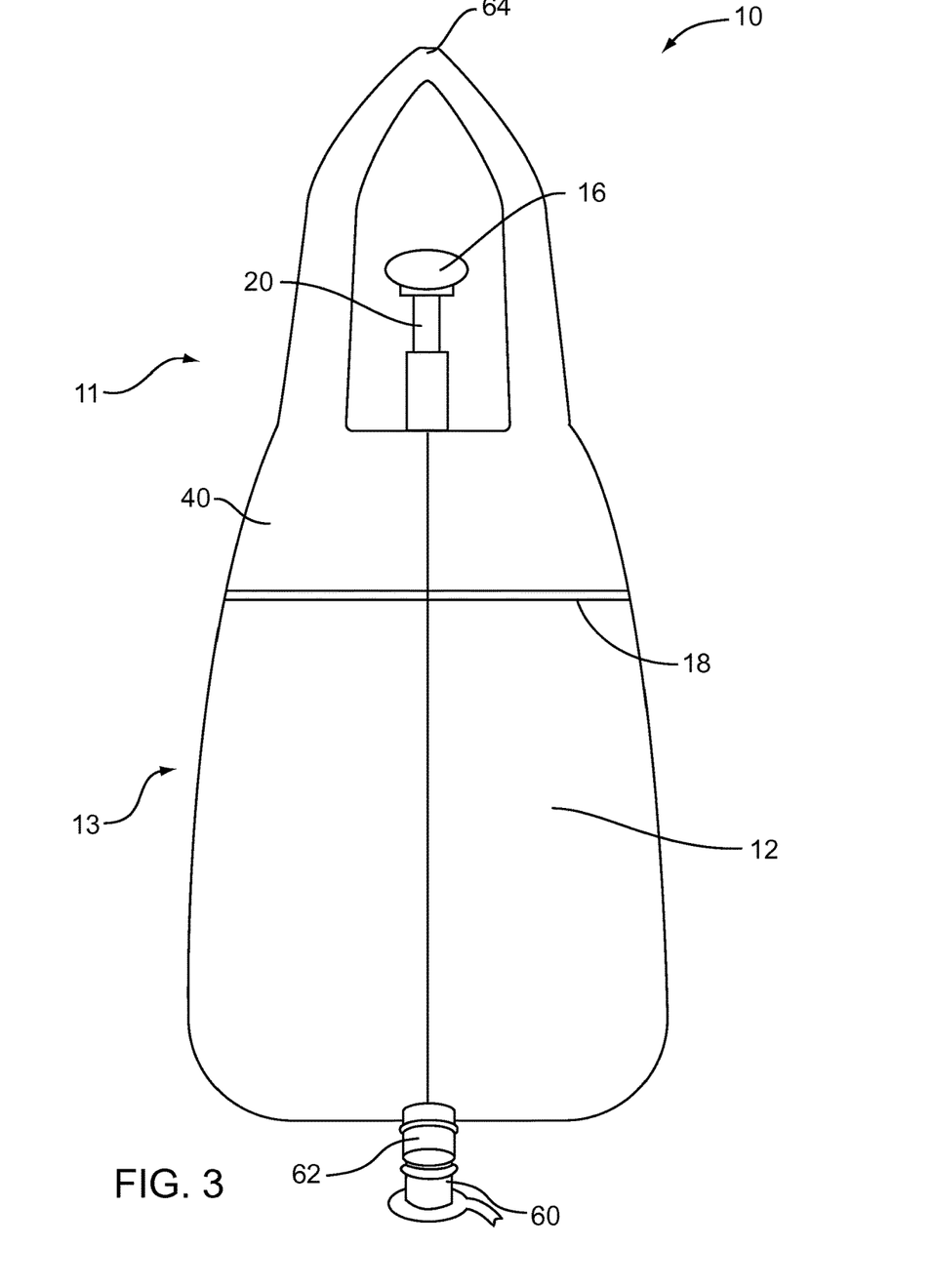
FIG. 3 is a side view of a multi-mix infusion bag.

Referring to the drawings, FIGS. 1 and 3 depicts a multi-mix infusion bag 10 in a stored condition, according to embodiments. The multi-mix infusion bag 10 comprises an upper portion 11 and a lower portion 13. The lower portion 13 comprises a main chamber 12. The upper portion 11 may comprise multiple compartments. For example, as shown, and without limitation, the upper portion 11 may include a first chamber 40, a second chamber 41, a third chamber 42, a fourth chamber 43, a fifth chamber 44 and a sixth chamber 45. The multi-mix infusion bag 10 comprises chamber separating members 17, to separate fluid agents 50, 51, 52, 53, 54 and 55, wherein first fluid agent 50 is held within first chamber 40, second fluid agent 51 is held within second chamber 41, third fluid agent 52 is held within third chamber 42, fourth fluid agent 53 is held within fourth chamber 43, fifth fluid agent 54 is held within fifth chamber 44, and sixth fluid agent 55 is held within sixth chamber 45. Additionally, the multi-mix infusion bag 10 may comprise a separating wall 18. The separating wall 18 separates the upper portion 11 from the lower portion 13 of the bag 10. The separating wall 18 serves to maintain the fluid agents 50-55 from entering lower chamber 12. The maintaining of the fluid agents 50-55 separate keeps the agents from reacting with one another until the appropriate time for the agents to be mixed. This increases shelf life. The first through sixth chambers 40-45 may each hold a predetermined amount of fluid. The separation of the fluid agents 50-55 constitutes the stored condition.

Further, within each upper chamber 40-45, the multi-mix infusion bag 10 may comprise interior dispensing devices. For example, a first dispensing device 20 corresponds to the first chamber 40, a second dispensing device 21 corresponds to the second chamber 41, a third dispensing device 42 corresponds to the third chamber 22, a fourth dispensing device 23 corresponds to the fourth chamber 43, a fifth dispensing device 24 corresponds to the fifth chamber 44, and a sixth dispensing device 25 corresponds to the sixth chamber 45. Each dispensing device 20-25 may be a plunger and include a perforating device. The first dispensing device 20 may include a first perforating device 30, the second dispensing device 21 may include a second perforating device 31, the third dispensing device 22 may include a third perforating device 32, the fourth dispensing device 23 may include a fourth perforating device 33, the fifth dispensing device 24 may include a fifth perforating device 34, and the sixth dispensing device 25 may include a sixth perforating device 35. As shown in FIG. 1, the dispensing devices 20-25 are in a stored position, wherein the fluid agents 50-55 are maintained in a separated condition.

The multi-mix infusion bag 10 may further include a dispensing bar 16, wherein the dispensing bar 16 couples the dispensing devices 20-25 together such that the dispensing bar 16 may be moved in a direction toward the lower portion 13 of the bag 10. Moving the dispensing bar 16 in the direction toward the lower portion 13 results in simultaneously activating each dispensing device 20-25 and moving each into a dispensing position. Accordingly, it should be understood that in some embodiments each dispensing device 20-25 may be activated independently, and in other embodiments, the dispensing devices 20-25 may be activated simultaneously.

Figure 2:
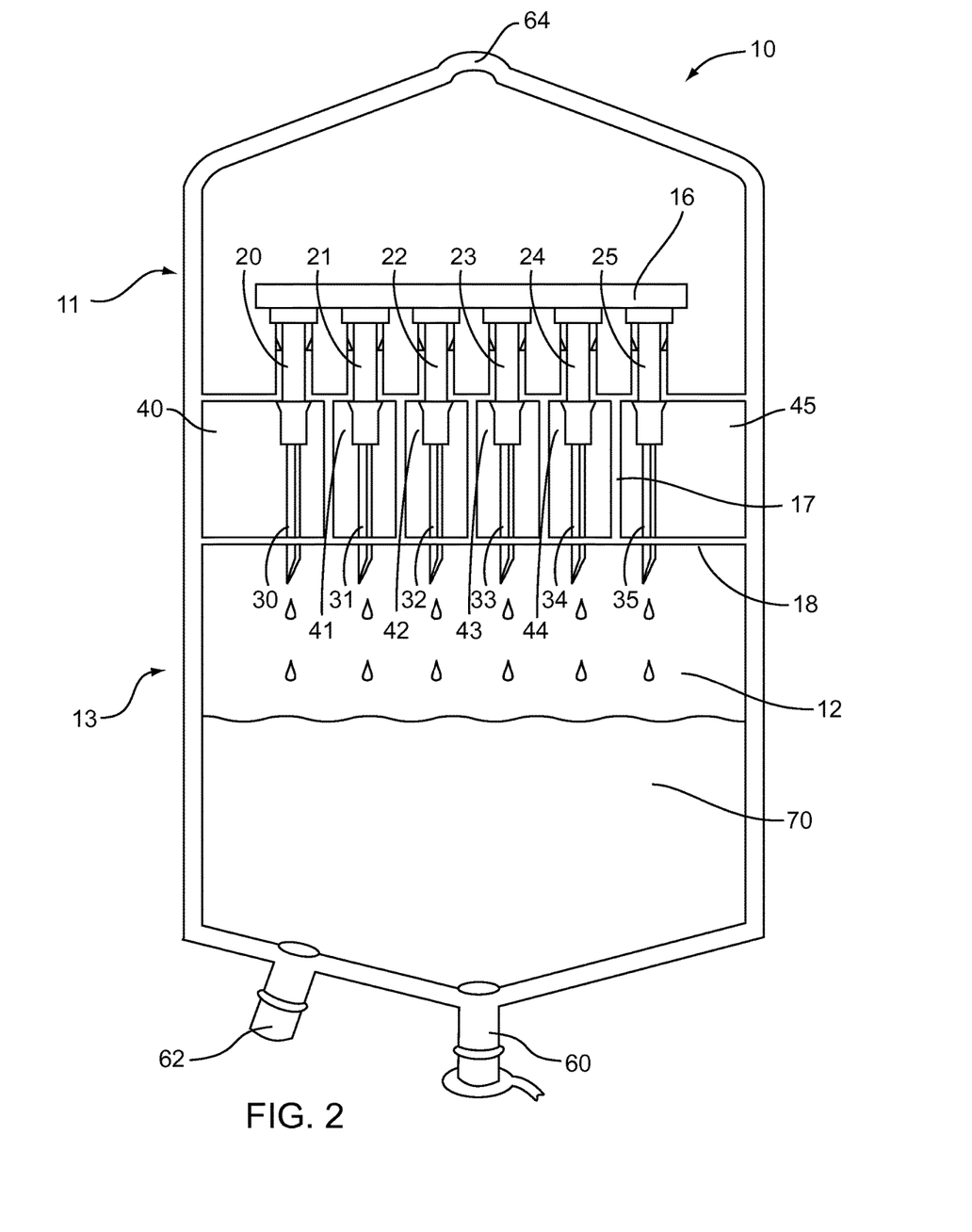
FIG. 2 is a front view of a multi-mix infusion bag with agents mixed together.

Referring again to the drawings, FIG. 2 depicts the multi-mix infusion bag 10 in a mixing condition according to embodiments. The dispensing devices 20-25 are shown in the dispensing position. When in the dispensing position, the dispensing devices 20-25 are each depressed toward the lower portion 13 of the bag 10.

In the order to dispense the fluid agents 50-55 into the lower portion 13 of the bag 10, plungers of each of the dispensing devices 20-25 are depressed toward the lower portion 13 of the bag 10 so that the point 92 of the needles 30-35 pierce the separating wall 18. The plungers may be depressed individually or may be depressed by applying pressure to the dispensing bar 16 which simultaneously forces all of the plungers into a depressed position. When depressed, the needles 30-35 have each pierced the separating wall 18. The needles 30-35 may each be a conduit, wherein the fluid agents 50-55 flow through the needles 30-35 respectively and enter into the lower chamber 12. When within the lower chamber 12, the fluid agents 50-55 are mixed together to form a mixed fluid 70 ready to be dispensed through outlet 60. Outlet 60 is configured to couple to known tubing for intravenously dispensing the mixed fluid 70 to a patient. During operation, it may be necessary to mix additional additives into the mixed fluid 70. Inlet 62 operates to allow the additional additives to enter the lower chamber 12 and be mixed with the mixed fluid 70. Further, hanger 64 may operate to operatively couple the bag 10 to a hanging device typically used to elevate infusion bags. In some embodiments, the lower chamber may be a size to hold at least the combined amount of fluid of the upper chambers.

Figure 4A:
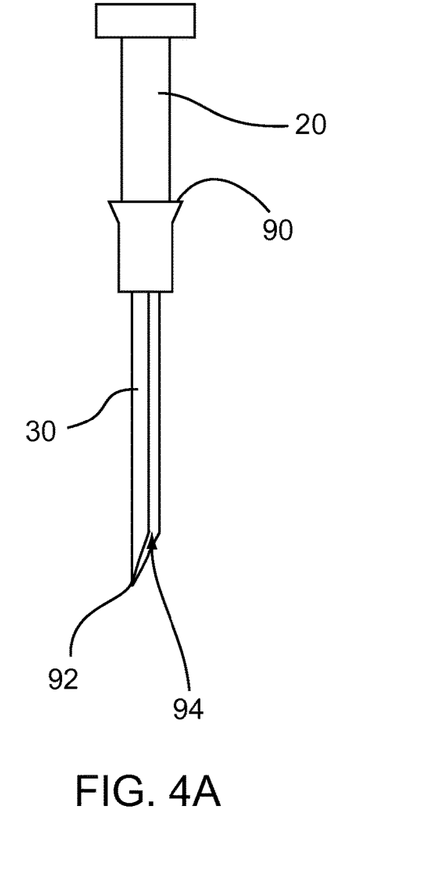
FIG. 4A is side view of a perforating device.
Figure 4B:
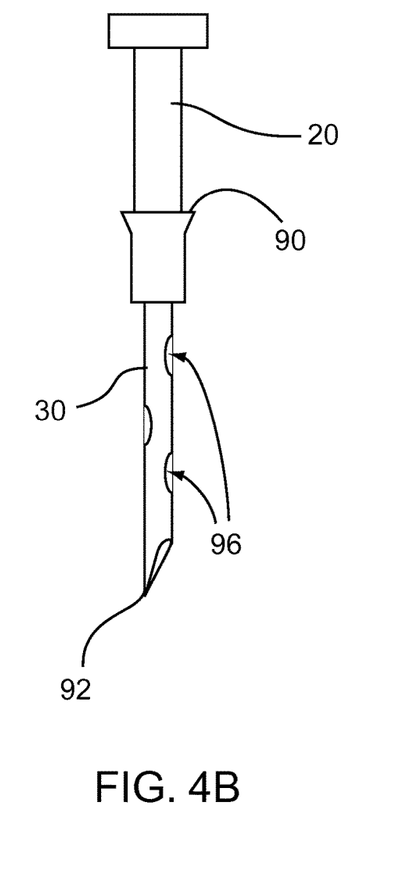
FIG. 4B is a side view of another perforating device.

As can be seen in FIGS. 4A-4B, dispensing devices 20-25 may include a plunger which may be the top portion of the dispensing devices 20-25. The plunger allows the dispensing devices 20-25 to be forced into a depressed or engaged location wherein the dispensing devices 20-25 are activated, allowing the fluid agents 50-55 to flow into the lower chamber 12 of the bag 10.

Additionally, dispensing devices 20-25 may include lip portion 90, wherein the lip portion 90 of each dispensing device 20-25 may engaged projections of a tube engagement with each upper chamber 40-45. The lip 90 inhibits removal of dispensing devices 20-25 once they are engaged within the tubes of the chambers 40-45.

Additionally, perforating devices 30-35 have various embodiments that are contemplated, such as, but not limited to a needle, a conduit and the like. For example each perforating device 30-35 may include a point 92 for puncturing the separation wall 18. Each perforating device 30-35 may also include a channel 94 wherein once the perforating device 30-35 punctures the separation wall 18. Channel 94 creates a fluid channel between upper chambers 40-45 and lower chamber 12. Fluid can then flow by gravity from the upper chambers 40-45 to the lower chamber 12. Other embodiments of needles 30-35 include a point 92 and a conduit perforating device having perforations 96 to allow fluid to enter the conduit portion and flow through an opening at the point 92. Fluid can them flow by gravity from the upper chambers 40-45 to the lower chamber 12. It will be understood that other types of needles may be used so long as a fluid communication between each of the upper chambers 40-45 and the lower chamber 12 is formed.

Figure 5A:
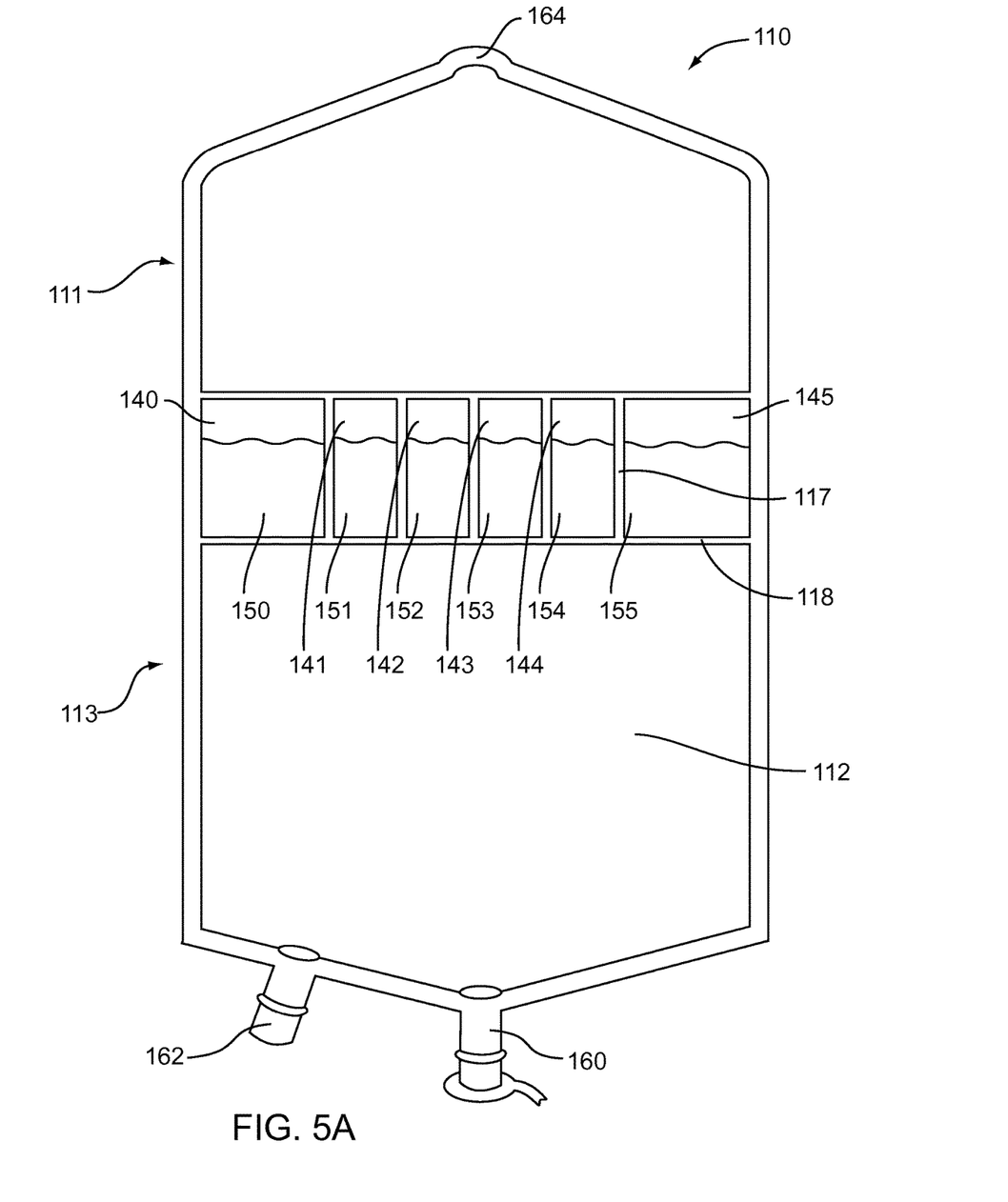
FIG. 5A is a front view of another multi-mix infusion bag with agents compartmentalized.

Referring to FIG. 5A another embodiment of a multi-mix infusion bag 110 in a stored condition, according to embodiments. The multi-mix infusion bag 110 comprises an upper portion 111 and a lower portion 113. The lower portion 113 comprises a main chamber 112. The upper portion 111 may comprise multiple compartments. For example, as shown, and without limitation, the upper portion 111 may include a first chamber 140, a second chamber 141, a third chamber 142, a fourth chamber 143, a fifth chamber 144 and a sixth chamber 145. The multi-mix infusion bag 110 comprises chamber separating members 117, to separate fluid agents 150, 151, 152, 153, 154 and 155, wherein first fluid agent 150 is held within first chamber 140, second fluid agent 151 is held within second chamber 141, third fluid agent 152 is held within third chamber 142, fourth fluid agent 153 is held within fourth chamber 143, fifth fluid agent 154 is held within fifth chamber 144, and sixth fluid agent 155 is held within sixth chamber 145. Additionally, the multi-mix infusion bag 110 may comprise a separating wall 118. The separating wall 118 separates the upper portion 111 from the lower portion 113 of the bag 110. The separating wall 118 serves to maintain the fluid agents 150-155 from entering lower chamber 112. The maintaining of the fluid agents 150-155 separate keeps the agents from reacting with one another until the appropriate time for the agents to be mixed.

This increases shelf life. The first through sixth chambers 140-145 may each hold a predetermined amount of fluid. The separation of the fluid agents 150-155 constitutes the stored condition.

Figure 5B:
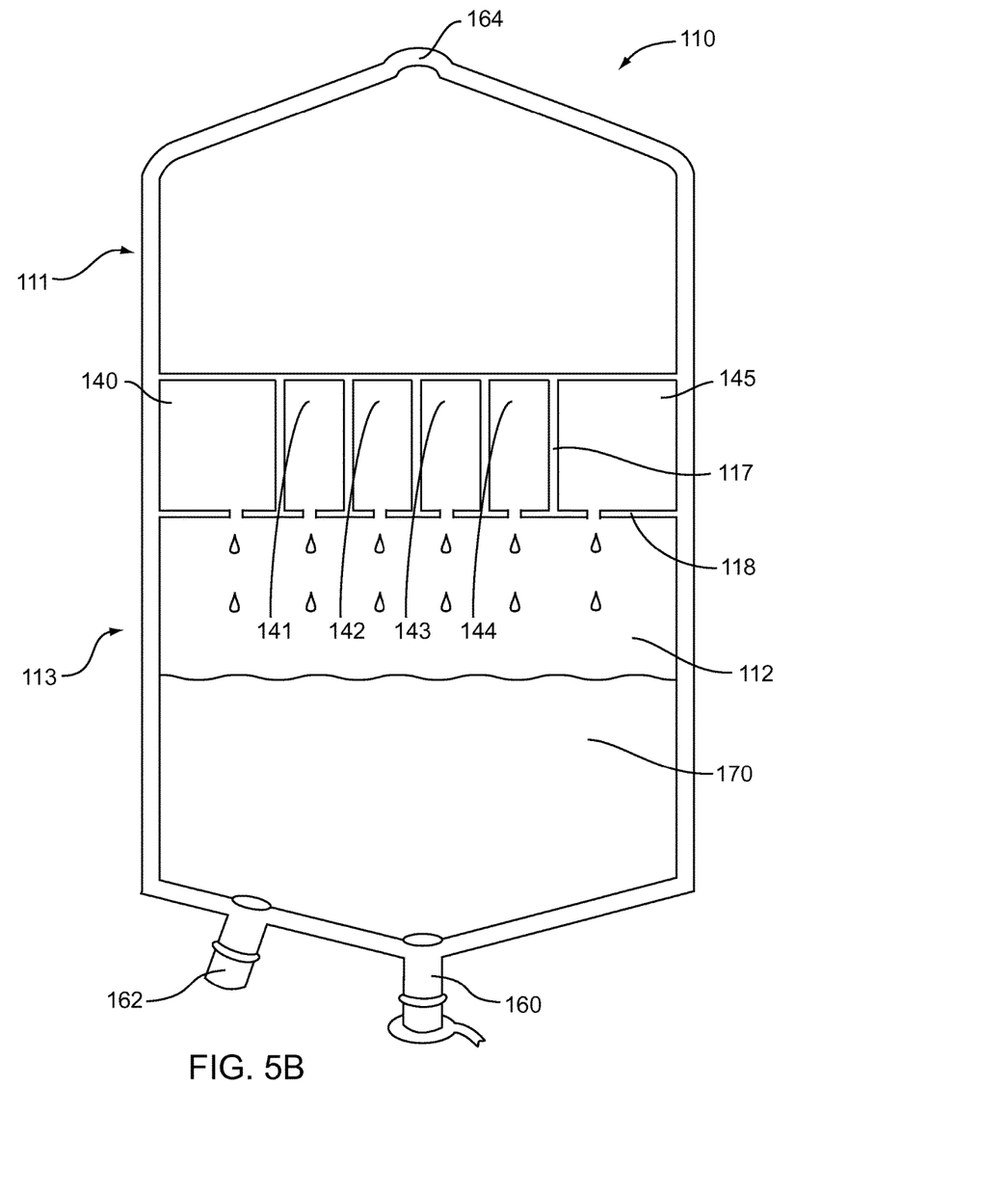
FIG. 5B is front view of another multi-mix infusion bag with agents mixed together.

FIG. 5B depicts the multi-mix infusion bag 110 in a mixing condition according to embodiments. The upper chambers 140-145 are shown in a dispensing position, wherein pressure is applied to each upper chamber 140-145 to form a perforation in separating wall 118. When in the dispensing position, the perforations in the separating wall 118 allow for the fluid agents 150-155 to flow through the perforations and enter into the lower chamber 112. When within the lower chamber 112, the fluid agents 150-155 are mixed together to form a mixed fluid 170 ready to be dispensed through outlet 160. Outlet 160 is configured to couple to known tubing for intravenously dispensing the mixed fluid 170 to a patient. During operation, it may be necessary to mix additional additives into the mixed fluid 170. Inlet 162 operates to allow the additional additives to enter the lower chamber 112 and be mixed with the mixed fluid 170. Further, hanger 164 may operate to operatively couple the bag 110 to a hanging device typically used to elevate infusion bags. In some embodiments, the lower chamber 112 may be a size to hold at least the combined amount of fluid of the upper chambers 140-145.

Figure 6A:
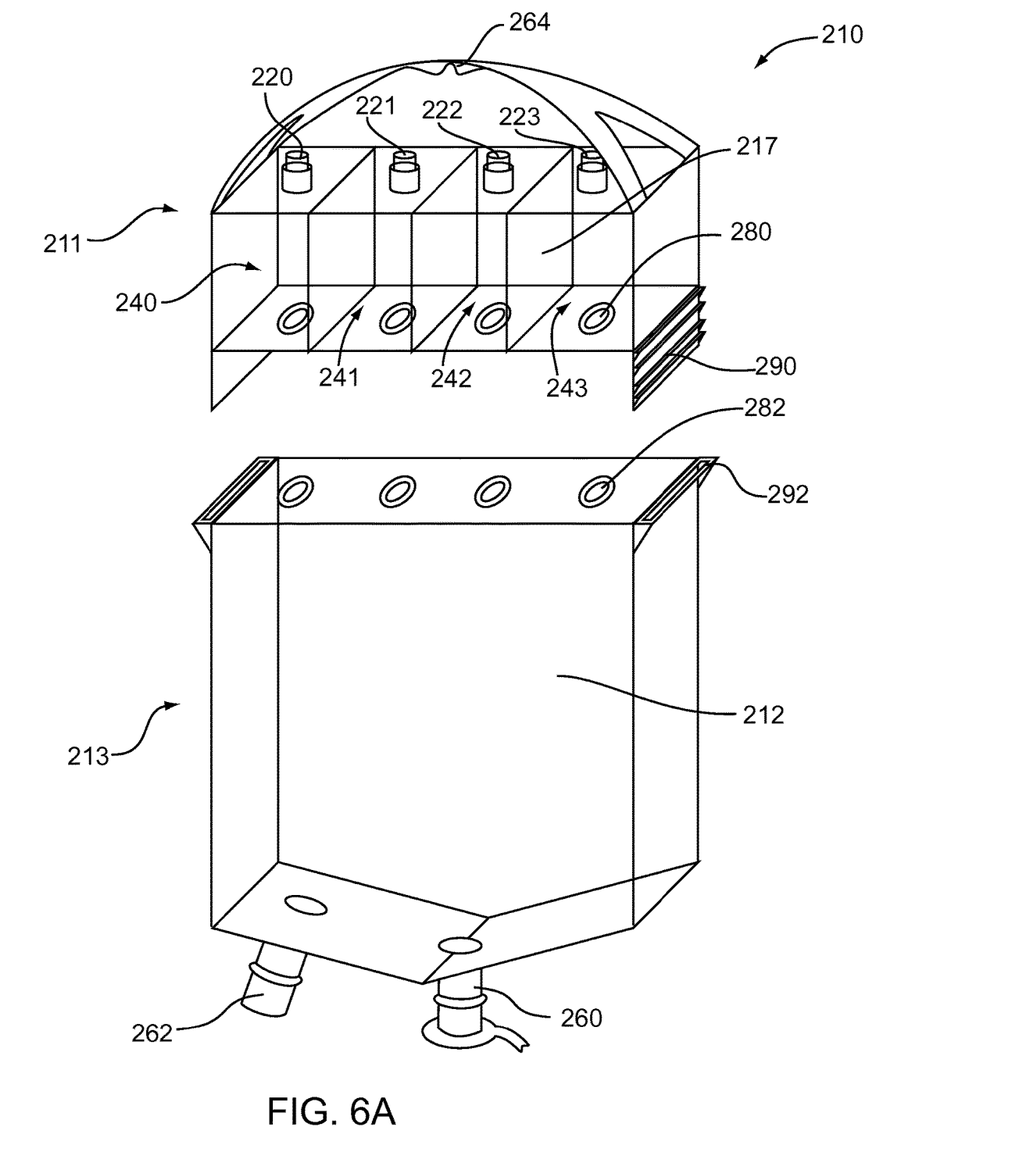
FIG. 6A is a perspective view of a multi-mix infusion bag with a separated upper section and lower section.

Referring to FIG. 6A another embodiment of a multi-mix infusion bag 210 in a stored condition, according to embodiments. The multi-mix infusion bag 210 comprises an upper portion 211 and a lower portion 213, wherein the upper portion 211 is separate from the lower portion 213. The lower portion 213 comprises a main chamber 212. The upper portion 211 may comprise multiple compartments, wherein the upper portion 211 may be coupled to the lower portion 213 in order to form a complete multi-mix infusion bag 210. For example, as shown, and without limitation, the upper portion 211 may include a first chamber 240, a second chamber 241, a third chamber 242, and a fourth chamber 243. The multi-mix infusion bag 210 comprises chamber separating members 217, to separate fluid agents held within each upper chamber 240-243. Each upper chamber 240-243 comprises an outlet portion 280, through which the separate fluid agents are dispensed.

Figure 6B:
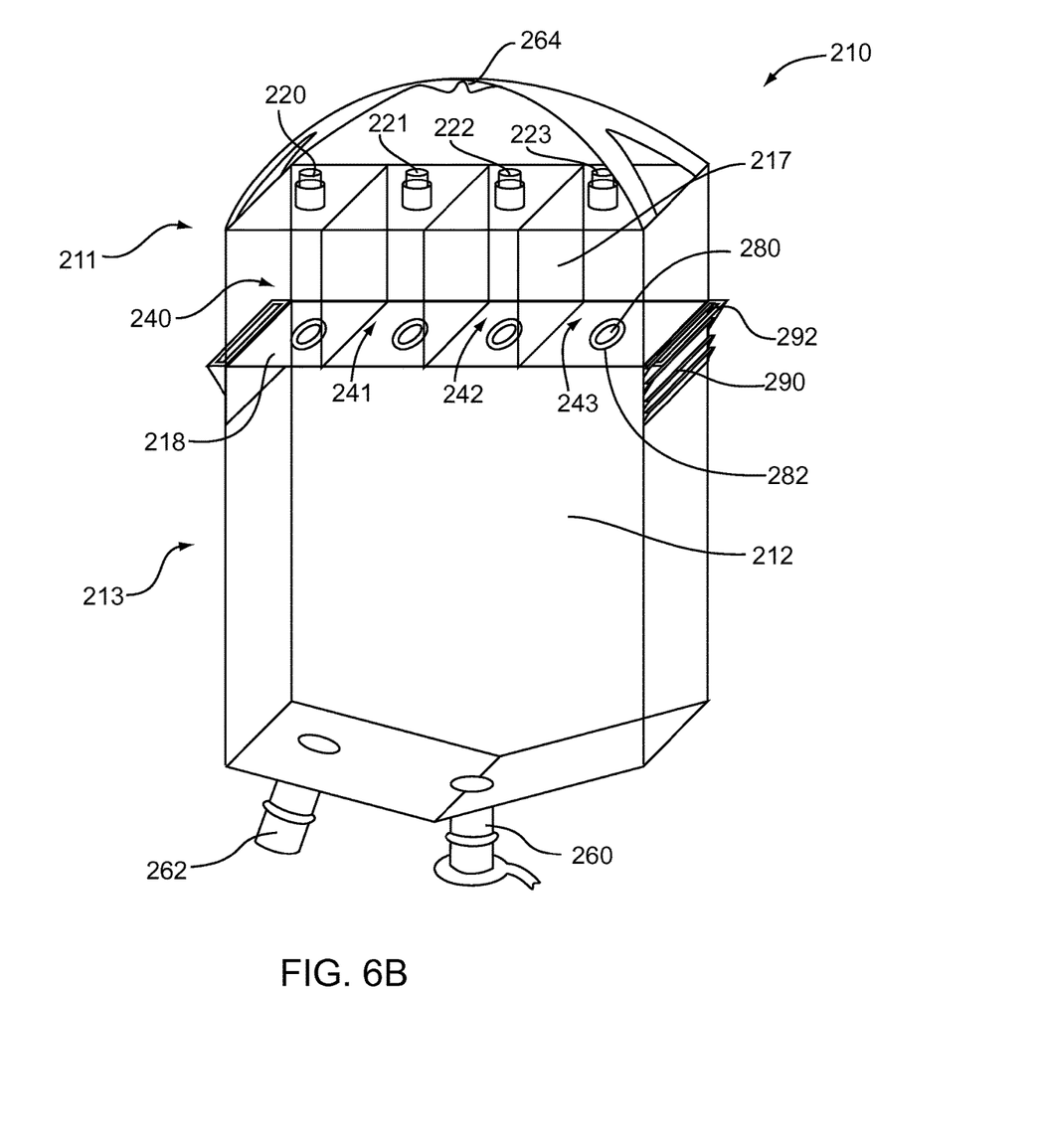
FIG. 6B is a perspective view of a multi-mix infusion bag with the separate upper section and lower section coupled together.

FIG. 6B depicts the multi-mix infusion bag 210 in a connected condition according to embodiments. The upper portion 211 includes a first connecting member 290 and the lower portion 213 includes a second connecting member 292. The first connecting member 290 may engaged the second connecting member 292 in order to couple the upper portion 211 to the lower portion 213. In some embodiments, the first connecting member 290 may be a tongue with pawls and the second connecting member 292 may be a groove receiver. It is understood that other connecting devices may be utilized, so long as the upper portion 211 is coupled to the lower portion 213. The upper chambers 240-243 are shown with outlet ports 280 engaging inlet ports 282 and a separating wall 218 is formed. With the outlet ports 280 engaging the inlet ports 282, the separated fluid agents may be transferred from the upper chambers 240-243 to the lower chamber 212 through the outlet ports 280 and inlet ports 282 by means previously described in FIGS. 1-3 and 5A-5B. During operation, it may be necessary to mix additional additives into the mixed fluid 170. Inlet 262 operates to allow the additional additives to enter the lower chamber 212 and be mixed with the mixed fluid 170. Further, hanger 264 may operate to operatively couple the bag 210 to a hanging device typically used to elevate infusion bags. In some embodiments, each upper chamber 240-243 may hold a predetermined amount of fluid, and the lower chamber 212 may be a size to hold at least the combined amount of fluid of the upper chambers 240-243.

While it has been shown in FIGS. 1-3 and 5A-5B that the multi-mix infusion bag comprises six chambers and FIGS. 6A-6B show 4 upper chambers, some embodiments may include two chambers, three chambers, four chambers, five chambers, six chambers, seven chambers, eight chambers or more. It may be contemplated that any number of chambers may be utilized in a multi-mix infusion bag.

Additionally, the multi-mix infusion bag may be amber in color and therefore impedes light and oxidation. The bag may be formed of silicone that is latex free, pvc free and DEHP free.

Figure 7:
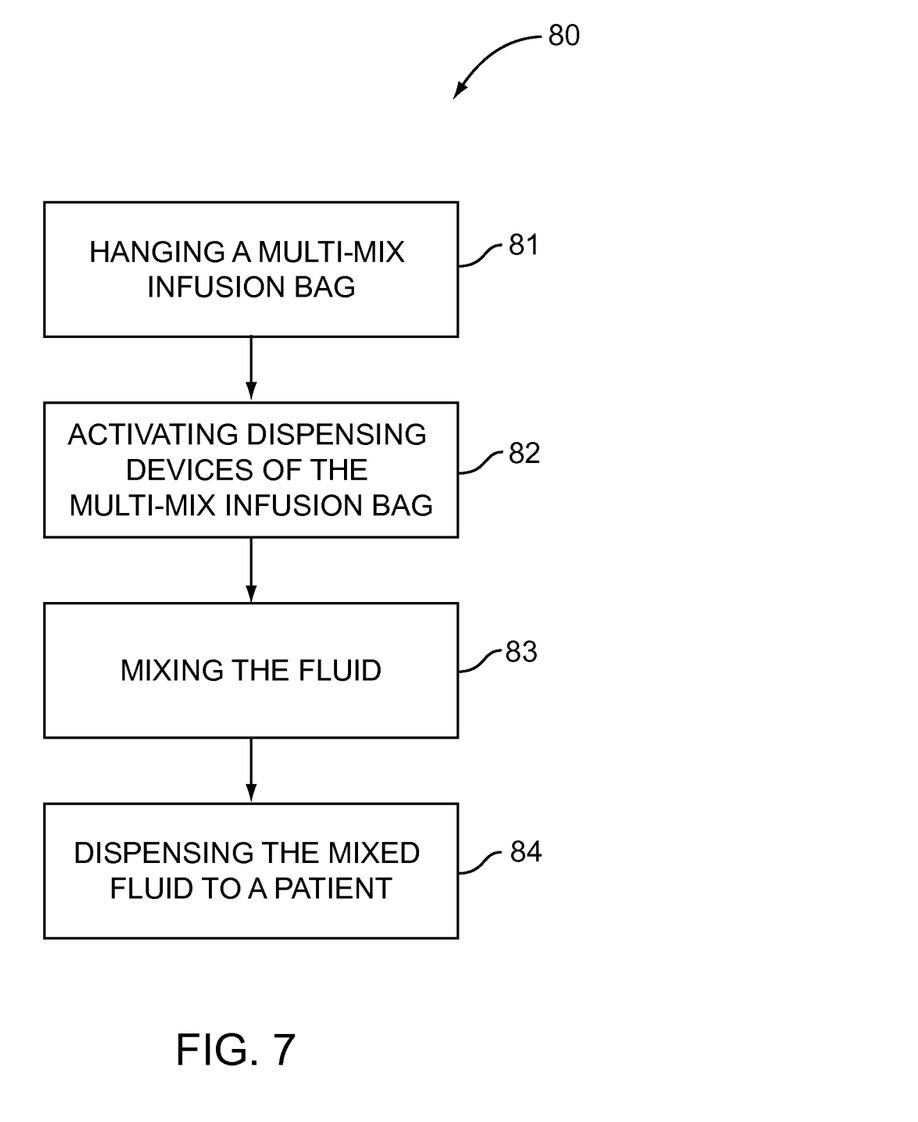
FIG. 7 is a flow chart of a method of operation of a multi-mix infusion bag.

Referring again to the drawings, FIG. 7 depicts a flow chart showing a method 80 of using a multi-mix infusion bag according to embodiments. The method 80 may include providing a multi-mix infusion bag having a plurality of chambers, wherein each chamber is pre-filled with a fluid agent (Step 81). The method may then include activating dispensing devices of the multi-mix infusion bag, wherein the fluid agent in each chamber is transferred into a lower chamber for mixing (Step 82). The fluid is then mixed (Step 83). Once the fluid is mixed, the method 80 includes dispensing the mixed fluid to a patient.

Step 82 of activating the dispensing devices may include independently activating each dispensing device. In other embodiments, activating the dispensing devices may include simultaneously activating all of the dispensing devices.

The method 80 may further include transferring an additive to the mixed fluid through an inlet of the multi-mix infusion bag. The method may also include impeding light and oxidation.

The embodiments and examples set forth herein were presented in order to best explain the present invention and its practical application and to thereby enable those of ordinary skill in the art to make and use the invention. However, those of ordinary skill in the art will recognize that the foregoing description and examples have been presented for the purposes of illustration and example only. The description as set forth is not intended to be exhaustive or to limit the invention to the precise form disclosed. Many modifications and variations are possible in light of the teachings above without departing from the spirit and scope of the forthcoming claims.

The invention claimed is:

1. A multi-mix infusion bag comprising:
   a lower portion having a lower chamber;
   an upper portion comprising a plurality of chambers, wherein each chamber is separated and contains a fluid agent, and wherein the multi-mix infusion bag is configured to transfer each fluid agent within each chamber of the upper portion into the lower chamber for mixing;
   a dispensing mechanism associated with each of the plurality of chambers, wherein the dispensing mechanism is in a top portion of each the plurality of chambers; and
   separating members located between each of the plurality of chambers, wherein each fluid agent is transferred from each of the plurality of chambers into the lower chamber in response to activation of the dispensing mechanism, wherein each dispensing mechanism comprises a dispensing device and a perforating device conduit, wherein the dispensing device comprises a plunging device, and wherein activation of the dispensing mechanism includes depressing the plunging device toward the lower portion of the bag.

2. The bag of claim 1, further comprising a separating wall located between the upper portion and the lower portion of the multi-mix infusion bag.

3. The bag of claim 1, wherein the perforating device conduit pierces the separating wall in response to depressing the dispensing device.

4. The bag of claim 1, further comprising a dispensing bar coupling each of the dispensing devices together, wherein the dispensing bar operates to depress each dispensing device simultaneously.

5. A multi-mix infusion bag comprising:
a lower portion having a lower chamber;
an upper portion comprising at least four chambers, wherein each chamber is separated and contains a fluid agent in a stored condition, and wherein the multi-mix infusion bag is moveable into a dispensing condition, wherein each fluid agent within each chamber of the upper portion is transferred into the lower chamber for mixing;
a dispensing mechanism associated with each of the at least four chambers, wherein the dispensing mechanism is in a top portion of each the at least four chambers; and
separating members located between each of the at least four chambers, wherein the fluid agent is transferred from the at least four chambers into the lower chamber in response to activation of the dispensing mechanism, wherein each dispensing mechanism comprises a dispensing device and a perforating device conduit, wherein the dispensing device comprises a plunging device, and wherein activation of the dispensing mechanism includes depressing the plunging device toward the lower portion of the bag.

6. The bag of claim 5, further comprising a separating wall located between the upper portion and the lower portion of the multi-mix infusion bag.

7. The bag of claim 5, wherein the perforating device conduit pierces the separating wall in response to depressing the dispensing device.

8. The bag of claim 5, further comprising a dispensing bar coupling each of the dispensing devices together, wherein the dispensing bar operates to depress each dispensing device simultaneously.

9. A method of using a multi-mix infusion bag, the method comprising:

hanging a multi-mix infusion bag having a plurality of chambers, wherein each chamber is pre-filled with a fluid agent in a stored condition;
activating dispensing devices in a top portion of each of the plurality of chambers of the multi-mix infusion bag to move the multi-mix infusion bag into a dispensing condition, wherein the fluid agent in each chamber is transferred into a lower chamber in response to activating the dispensing devices, wherein activating dispensing devices further comprises piercing a separating wall with a perforating device conduit of each dispensing device;
mixing the fluid agents to form a mixed fluid; and
dispensing the mixed fluid to a patient.

10. The method of claim 9, wherein activating dispensing devices further comprises independently activating each dispensing device.

11. The method of claim 9, wherein activating dispensing devices further comprises simultaneously activating each dispensing device.

12. The method of claim 9, further comprising transferring an additive to the mixed fluid through an inlet of the multi-mix infusion bag.

13. The method of claim 9, further comprising impeding light and oxidation.

14. A multi-mix infusion bag comprising:
a lower portion having a lower chamber;
an upper portion comprising a plurality of chambers, wherein each chamber is separated and contains a fluid agent, and wherein the multi-mix infusion bag is configured to transfer each fluid agent within each chamber of the upper portion into the lower chamber for mixing;
separating members located between each of the plurality of chambers;
a dispensing mechanism associated with each chamber of the upper portion, wherein each fluid agent is transferred from each of the plurality of chambers into the lower chamber in response to activation of the dispensing mechanism, wherein each dispensing mechanism comprises a dispensing device and a perforating device conduit, wherein activation of the dispensing mechanism includes depressing the dispensing device toward the lower portion of the bag; and
a dispensing bar coupling each of the dispensing devices together, wherein the dispensing bar operates to depress each dispensing device simultaneously.

* * * * *